(12) United States Patent
Stahl et al.

(10) Patent No.: US 8,591,919 B2
(45) Date of Patent: Nov. 26, 2013

(54) SYNERGISTIC MIXTURE OF BETA-GALACTO-OLIGOSACCHARIDES WITH BETA-1,3 AND BETA -1,4/1,6 LINKAGES

(75) Inventors: Bernd Stahl, Rosbach-Rodheim (DE); Alma Jildou Nauta, Driebergen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 13/377,464

(22) PCT Filed: Jun. 14, 2010

(86) PCT No.: PCT/NL2010/050364
§ 371 (c)(1),
(2), (4) Date: Feb. 17, 2012

(87) PCT Pub. No.: WO2010/143961
PCT Pub. Date: Dec. 16, 2010

(65) Prior Publication Data
US 2012/0141541 A1     Jun. 7, 2012

(30) Foreign Application Priority Data
Jun. 12, 2009   (WO) ................ PCT/NL2009/050331

(51) Int. Cl.
*A61K 31/738* (2006.01)
(52) U.S. Cl.
USPC ..................................... 424/278.1
(58) Field of Classification Search
None
See application file for complete search history.

(56) References Cited

FOREIGN PATENT DOCUMENTS

| | | |
|---|---|---|
| EP | 1 644 482 B1 | 4/2004 |
| WO | WO-01/64225 A1 | 9/2001 |
| WO | WO-2005/003329 A1 | 1/2005 |
| WO | WO-2006/115412 A2 | 11/2006 |
| WO | WO-2005/039597 A2 | 4/2007 |
| WO | WO-2007/067053 A1 | 6/2007 |
| WO | WO-2007/101675 A1 | 9/2007 |

OTHER PUBLICATIONS

Osborn et al. (Cochrane Database of Systematic Rev., 4:1-33, 2007).*
Tzortzis, et al., "A Novel Galactooligosaccharide Mixture Increases the Bifidobacterial Population Numbrs in a Continuous In Vitro Fermentation System and in the Proximal Colonic Contents of Pigs In Vivo," The Journal of Nutrition, (2005), vol. 135, pp. 1726-1731, XP002562891.
Vulevic, et al., "Modulation of the fecal microflora profile and immune function by a novel trans-galactooligosaccharide mixture (B-GOS) in healthy elderly volunteers," American Journal of Clinical Nutirition, (2008), vol. 88, pp. 1438-1446, XP008117002
Search Report in International Application No. PCT/NL2010/050364 mailed Aug. 4, 2010.

* cited by examiner

*Primary Examiner* — Brian J Gangle
(74) *Attorney, Agent, or Firm* — Gilberto M. Villacorta; Sunit Talapatra; Foley & Lardner LLP

(57) ABSTRACT

The present invention relates to a nutritional composition comprising at least two different beta-galacto-oligosaccharides (BGOS) A and B wherein the majority of linkages between two galactose residues in BGOS A are beta 1,4 and/or beta 1,6, and the majority of linkages between two galactose residues in BGOS B are beta 1,3. Such mixtures show superior effects on the immune system and are particularly suitable for infant nutrition.

22 Claims, No Drawings

SYNERGISTIC MIXTURE OF BETA-GALACTO-OLIGOSACCHARIDES WITH BETA-1,3 AND BETA -1,4/1,6 LINKAGES

FIELD OF THE INVENTION

The present invention relates to nutritional compositions comprising two structurally different beta-galacto-oligosaccharides. This mixture is especially suitable for infant nutrition.

BACKGROUND OF THE INVENTION

Non-digestible oligosaccharides (NDO) are a major constituent of human milk. Human NDO promote the growth of a beneficial microbiota dominated by bifidobacteria. Some human NDO are also known to be able to prevent directly the adhesion of pathogens and toxins. The presence of a microbiota rich in bifidobacteria is associated with a reduced risk on atopic diseases such as atopic dermatitis, food allergy and asthma and in a reduced risk on infections with pathogens. Non-digestible oligosaccharides (NDO) are therefore thought responsible for the lower incidence of infections and of atopic diseases observed in human milk fed infants compared with formula fed infants. NDO are an important factor in the innate immune system in human milk, whereby the mother protects the infants, which have a naive and immature acquired immune system and a not yet fully developed innate immune system.

Human milk is the preferred food for infants. However, it is not always possible or desirable to breast feed an infant. In such cases infant formulae or follow on formulae are a good alternative. These formulae should have an optimal composition in order to mimic the beneficial effects of breast milk as close as possible. This optimal composition includes the presence of NDO.

WO 2007/067053 discloses an infant formula comprising the plant-derived prebiotics inulin and galacturonic acid oligosaccharide and the from lactose synthesized prebiotic transgalacto-oligosaccharide to reduce infections.

WO 2005/039597 relates to the use of acid oligosaccharide and neutral oligosaccharide for enhancing the immune system and the treatment and/or prevention of immune system related disorders.

WO 01/642255 relates to a nutritional composition comprising a prebiotic for enhancement of an immune response.

EP 1 644 482 relates to novel strains of *Bifidobacterium bifidum* capable of producing a novel galactosidase enzyme activity that converts lactose to a novel mixture of galacto-oligosaccharides. The mixture of oligosaccharides may be incorporated into numerous food products or animal feeds for improving gut health by promoting the growth of bifidobacteria in the gut, and repressing the growth of the pathogenic microflora.

Many infant formulae are known to comprise NDO, still further improvements can be made regarding mixtures of NDO having an improved effect on the intestinal microbiota and/or the innate immune system.

SUMMARY OF THE INVENTION

The inventors surprisingly found that a mixture of beta-1,3 galacto-oligosaccharides and beta-1,4 and/or 1,6 galacto-oligosaccharides and preferably also fructo-oligosaccharides, has an improved effect on stimulating the immune system, compared to the single components. An increased vaccination response, indicative for an increased Th1 response was observed.

The present combination is therefore especially advantageous for human subjects having a reduced Th1 response in comparison with healthy adults, in particular newborn infants. The present combination is suitable for treatment and/or prevention of infections, and/or for supporting vaccination response before, during and/or after vaccination. The present combination is especially suitable for the treatment and/or prevention of diseases which can be prevented and/or treated by an increase in Th1 response and/or of Th1/Th2 balance, in particular allergy, atopic dermatitis, asthma, food allergy, allergic rhinitis (e.g. pollen allergy), dust mite allergy and other forms of hypersensitivity like systemic anaphylaxis and acute urticaria.

DETAILED DESCRIPTION

The present invention thus concerns a nutritional composition comprising at least two different beta-galacto-oligosaccharides (BGOS) A and B wherein a) BGOS A has the structure of $Gal_n$-Glu and/or $Gal_m$, with n=2 to 6 and m=2 to 7 and comprises at least 80% of the sum of beta 1,4 and beta 1,6 linkages between two galactose residues, based on the total number of linkages between galactose residues, and b) BGOS B has the structure of $Gal_n$-Glu and/or $Gal_m$, with n=2 to 6 and m=2 to 7 and comprises at least 80% beta 1,3 linkages between two galactose residues, based on total linkages and c) the weight ratio between BGOS A and BGOS B is from 1 to 5.

Beta-Galacto-Oligosaccharides

The present invention relates to a nutritional composition comprising at least two different beta-galacto-oligosaccharides A and B wherein A has the structure of $Gal_n$-Glu and/or $Gal_m$, with n=2 to 6 and m=2 to 7 and comprises at least 80% of the sum of beta 1,4 and beta 1,6 linkages between two galactose residues, based on total linkages, and wherein B has the structure of $Gal_n$-Glu and/or $Gal_m$, with n=2 to 6 and m=2 to 7 and comprises at least 80% beta 1,3 linkages between two galactose residues, based on the total number of linkages between galactose residues and wherein the weight ratio between A and B is from 1 to 5, more preferably from 1.25 to 4, even more preferable from 1.5 to 3.5. As an example Gal-Gal and Gal-Gal-Glu have a % linkages between two galactose residues of either 0% or 100% beta 1,3, or 0% or 100% beta 1,4, or 0% or 100% beta 1,6. Further, Gal-Gal-Gal and Gal-Gal-Gal-Glu have a % linkages between two galactose residues of either 0% or 50% or 100% beta 1,3, or 0% or 50% or 100% beta 1,4, or 0% or 50% or 100% beta 1,6. As an example it is further noted that Gal-Gal-Gal or Gal-Gal-Gal-Glu can have a % linkages between two galactose residues of 50% beta 1,4 and 50% beta 1,6. Such an oligosaccharide falls under the definition of BGOS A.

Herein the "at least two different beta-galacto-oligosaccharides A and B" as described above is also referred to as "combination of BGOS A and B". Herein beta-galacto-oligosaccharides (BGOS) may also be referred to as transgalacto-oligosaccharides (TOS). BGOS and TOS are considered synonyms. BGOS is defined as an oligosaccharide of at least two galactose monose units which are linked together via a beta linkage. Optionally at the terminal end one terminal glucose unit is present. BGOS according to the present invention has a degree of polymerization (DP) of 2 to 7.

A suitable way to form BGOS is to treat lactose with beta-galactosidase. Dependent on the specificity of the enzyme used, a galactose unit is hydrolysed from lactose and coupled to another lactose unit via a beta-linkage to form a trisaccharide. A galactose unit may also be coupled to another single galactose unit to form a disaccharide. Subsequent galactose units are coupled to form oligosaccharides. The majority of such formed oligosaccharides have a DP of 7 or lower.

A suitable way to prepare beta-1,6 and or beta-1,4 GOS, BGOS A, is by using the beta-galactosidase from *Bacillus circulars*. A commercially available source of BGOS is VIVI-NAL®-TOS form Borculo Domo, The Netherlands. VIVI-NAL®-GOS comprises BGOS mainly with beta1.4 and b1,6 linkages.

A suitable way to produce beta-1,3 GOS, BGOS B, is by using the beta-galacosidase from *S. thermophilus*. In particular using beta-galacosidase from strain CNCM I 1470 and/or CNCM I 1650 in a process as disclosed in example 4 of FR2723960 or example 6 of EP0778885 is suitable. *S. thermophilus* CNCM I-1620 was deposited under the Budapest Treaty on 23 Aug. 1995 at Collection Nationale de Cultures de Microorganisms van Institute Pasteur, Paris, France by Compagnie Gervais Danone. *S. thermophilus* CNCM I-1470 was deposited under the Budapest Treaty on 25 Aug. 1994 at Collection Nationale de Cultures de Microorganisms van Institute Pasteur, Paris, France by Compagnie Gervais Danone. Both strains have also been published in WO 96/06924.

The BGOS of the present invention are non-digestible. No human digestive enzymes (including human lactase) are able to hydrolyse BGOS. BGOS when consumed therefore reaches the large intestine intact and is available for fermentation by the intestinal microbiotia.

Both BGOS A and B should be present in sufficient amounts relative to each other. Furthermore, BGOS B should be present in lower amounts compared to BGOS A, since the NDO in human milk are more predominant in beta 1,4 and beta 1,6 glycosidic linkages than in beta 1,3 glycosidic linkages. A mixture of BGOS A and BGOS B with a relatively lower amount of BGOS B showed an improved effect on the immune system. Therefore, the weight ratio between A and B is from 1 to 5, more preferably from 1.25 to 4, even more preferably from 1.5 to 3.5. Such a weight ratio ensures an optimal improved effect of the mixture of BGOS A and B.

Preferably the nutritional composition according to the present invention comprises at least 250 mg of the sum of BGOS A and B per 100 ml, more preferably at least 400 even more preferably at least 600 mg. Preferably the composition does not comprise more than 2500 mg of the sum of BGOS A and B per 100 ml, more preferably not more than 1500 mg. Preferably the nutritional composition according to the present invention comprises at least 1 wt. % of the sum of BGOS A and B based on dry weight, more preferably at least 2 wt. %, even more preferably at least 4 wt. %. Preferably the composition does not comprise more than 20 wt. % of the sum of BGOS A and B based on dry weight of the total composition, more preferably not more than 10 wt. %. Lower amounts result in less effective composition, whereas the presence of higher amounts of BGOS may result in side-effects such as osmotic disturbances, abdominal pain, bloating, gas formation and/or flatulence Preferably the composition according to the present invention also comprises fructo-oligosaccharides (FOS). Preferably the preparation obtained by the present process comprises fructo-oligosaccharides. Fructo-oligosaccharides as used in the present invention refers to carbohydrates composed of over 50%, preferably over 65% fructose units based on monomeric subunits, in which at least 50%, more preferably at least 75%, even more preferably at least 90%, of the fructose units are linked together via a beta-glycosidic linkage, preferably a beta-2,1 glycosidic linkage. A glucose unit may be present at the reducing end of the chain of fructose units. Preferably the fructo-oligosaccharide has a DP or average DP in the range of 2 to 250, more preferably 2 to 100, even more preferably 10 to 60. Fructo-oligosaccharide comprises levan, hydrolysed levan, inulin, hydrolysed inulin, and synthesised fructo-oligosaccharides. Preferably the preparation comprises short chain fructo-oligosaccharides with an average degree of polymerization (DP) of 3 to 6, more preferably hydrolysed inulin or synthetic fructo-oligosaccharide. Preferably the preparation comprises long chain fructo-oligosaccharides with an average DP above 20. Preferably the preparation comprises both short chain and long chain fructo-oligosaccharides. Fructo-oligosaccharide suitable for use in the process of the invention is also readily commercially available, e.g. RaftilineHP (Orafti). Preferably the nutritional composition according to the present invention comprises at least 25 mg FOS per 100 ml, more preferably at least 40 even more preferably at least 60 mg. Preferably the composition does not comprise more than 250 mg FOS per 100 ml, more preferably not more than 150 mg. Preferably the nutritional composition according to the present invention comprises at least 0.15 wt. % FOS based on dry weight, more preferably at least 0.25 wt. %, even more preferably at least 0.4 wt. %. Preferably the composition does not comprise more than 1.5 wt. % FOS based on dry weight of the total composition, more preferably not more than 1 wt. %. The presence of FOS shows a further improved effect on the immune system.

Nutritional Composition

The present combination of BGOS A and B is preferably present in a nutritional composition. The composition of the present invention is not human milk. The present composition is preferably enterally administered, more preferably orally.

The present composition is preferably a nutritional formula, preferably an infant formula. The present composition can be advantageously applied as a complete nutrition for infants. The present composition preferably comprises lipid, protein and digestible carbohydrate and is preferably administered in liquid form. The present invention includes dry food, preferably a. powders which is accompanied with instructions as to admix said dry food mixture with a suitable liquid, preferably with water.

The present invention advantageously provides a composition wherein the lipid provides 5 to 50% of the total calories, the protein provides 5 to 50% of the total calories, and the digestible carbohydrate provides 15 to 85% of the total calories. The present invention advantageously provides a composition wherein the lipid provides 20 to 50% of the total calories, the protein provides 5 to 30% of the total calories, and the digestible carbohydrate provides 30 to 70% of the total calories. Preferably, in the present composition the lipid provides 35 to 50% of the total calories, the protein provides 7.5 to 12.5% of the total calories, and the digestible carbohydrate provides 40 to 55% of the total calories. For calculation of the % of total calories for the protein, the total of energy provided by the proteins, peptides and amino acids needs to be taken into account.

The present composition preferably comprises at least one lipid selected from the group consisting of animal lipid, excluding human lipids, and vegetable lipids. Preferably the present composition comprises a combination of vegetable lipids and at least one oil selected from the group consisting of fish oil, animal oil, algae oil, fungal oil, and bacterial oil. The present composition preferably comprises long chain polyunsaturated fatty acids (LC-PUFA). LC-PUFA are fatty acids or fatty acyl chains with a length of 20 to 24 carbon atoms, preferably 20 or 22 carbon atoms comprising two or more unsaturated bonds. The LC-PUFA may be provided as free fatty acids, in triglyceride form, in diglyceride form, in monoglyceride form, in phospholipid form, or as a mixture of one of more of the above.

The protein used in the nutritional composition is preferably selected from the group consisting of non-human animal proteins (preferably milk proteins), vegetable proteins (preferably soy protein and/or rice protein), hydrolysates thereof, free amino acids and mixtures thereof. The present composition preferably contains casein, whey, hydrolyzed casein and/or hydrolyzed whey protein. Preferably the protein comprises intact proteins, more preferably intact bovine whey proteins and/or intact bovine casein proteins.

The present composition preferably contains digestible carbohydrates selected from the group consisting of sucrose, lactose, glucose, fructose, corn syrup solids, starch and maltodextrins, more preferably lactose.

Preferably the composition comprises *Bifidobacterium breve*. *Bifidobacterium breve* is a Gram-positive, anaerobic, branched rod-shaped bacterium. The present *B. breve* preferably has at least 95% identity with the 16 S rRNA sequence when compared to the type strain of *B. breve* ATCC 15700, more preferably at least 97% identity (Stackebrandt & Goebel, 1994, *Int. J. Syst. Bacteriol.* 44:846-849).

Preferred *B. breve* strains are those isolated from the faeces of healthy human milk-fed infants. Typically, these are commercially available from producers of lactic acid bacteria, but they can also directly be isolated from faeces, identified, characterised and produced. The *B. breve* may be viable or non viable. According to a preferred embodiment, the *B. breve* is strain *B. breve* CNCM I-2219 deposited under the Budapest Treaty on 31 May 1999 at Collection Nationale de Cultures de Microorganisms (CNCM) in Paris, France by Compagnie Gervais Danone as published in EP 1189517. It was found that the presence of this stain resulted in a further improvement of the vaccination response.

The present composition preferably comprises an amount of viable and/or non-viable *Bifidobacterium breve*. In case of viable *B. breve*, an amount of at least $10^3$ colony forming units (cfu) per g dry weight of the composition, or, in case of non-viable *B. breve*, an amount equivalent to at least $10^3$ cfu per g dry weight of the composition is preferably present. The present composition preferably comprises $10^3$ to $10^{13}$ cfu *B. Breve* or in case of non-viable *B. Breve* $10^3$ to $10^{13}$ equivalence of cfu per gram dry weight of the present composition, preferably $10^4$ to $10^{12}$, more preferably $10^5$ to $10^{11}$, most preferably $10^5$ to $10^{10}$ cfu, or equivalence of cfu, *B. breve* per gram dry weight of the present composition. An amount of non-viable *Bifidobacterium breve* equivalent to at least $10^3$ cfu per g dry weight means non-viable *Bifidobacterium breve* in an amount which is the equivalence of an amount of at least $10^3$ cfu viable *B. breve* per g dry weight.

The equivalent of cfu can be determined by performing the 5'nuclease assay with the *B. breve* probes and primers as disclosed in WO 2005039319 in the product (i.e. an infant formula) comprising non-viable *B. breve* and compare this with a calibration curve obtained from a comparable product (for instance a standard infant formula) to which known amounts of dried, viable *B. breve* cfu have been added. The dried viable bifidobacteria can be commercially obtained as described above. The value of cfu in the calibration curve made by living *B. breve* which has same 5'nuclease assay response as the product comprising the inactivated *B. breve* is considered to be the equivalent amount in cfu of non-viable *B. breve*. Alternatively, the amount of cfu per g dry weight can be determined in a composition just before the inactivation step. Preferably the *B. breve* is heat-killed.

It is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

The nutritional composition of the present invention is preferably is in liquid form. It preferably has a limited viscosity so it can be applied as e.g. liquid baby foods and liquid clinical food which can be fed through a teat, a tube or a straw, while retaining the low viscosity. In a preferred embodiment, the present composition has a viscosity below 600 mPa·s, preferably below 250 mPas, more preferably below 60 mPa·s, even more preferably below 35 mPa·s, most preferably below 6 mPa·s, at a shear rate of 100 $s^{-1}$ at 20° C. Whenever the term viscosity used in the present document, this refers to the physical parameter which is determined according to the following method: The viscosity may be determined using a Carri-Med CSL rheometer. The used geometry is of conical shape (6 cm 2 deg acrylic cone) and the gap between plate and geometry is set on 55 um. A linear continuous ramp shear rate is used from 0 to 150 $s^{-1}$ in 20 seconds. It is noted that a composition in powder form with the instruction to prepare an aqueous solution, e.g. by adding water in a certain ratio and which then results in a viscosity as specified is also encompassed by the invention.

Application

The present combination of BGOS A and B was found to synergistically stimulate the immune-system. In particular the vaccination response was increased, which is indicative of increased Th1 response. The effect of the combination of these two components is higher than the effects of the single components.

The present combination can advantageously be used in the treatment and/or prevention of a disease, and thus the invention concerns a method for the treatment and/or prevention of a disease in a mammal, said method comprising administering the present composition comprising BGOS A and B to the mammal. In other words, the invention also concerns the use of a composition comprising BGOS A and B according to the present invention for the manufacture of a composition, preferably a nutritional composition, for the treatment and/or prevention of a disease. In other words the invention concerns a composition or nutritional composition comprising a composition comprising BGOS A and B according to the present invention for use in the treatment and/or prevention of a disease. Preferably the mammal is a human, even more preferably a human infant. Thus the invention also concerns the use of a composition comprising BGOS A and B according to the present invention for the manufacture of a composition, preferably a nutritional composition, for the treatment and/or prevention of a disease in an infant. Or in other words the invention concerns a composition or nutritional composition comprising BGOS A and B according to the present invention for use in the treatment and/or prevention of a disease in an infant.

In the context of this invention, an infant is in the age of 0 to 6 years, preferably in the age of 0 to 4 years, preferably in the age of 0 to 2 years, preferably in the age of 0 to 1 year.

Also the invention concerns a method for providing nutrition to an infant, said method comprising administering the present composition comprising BGOS A and B to the infant. In other words, the invention also concerns the use of a composition comprising BGOS A and B according to the present invention for the manufacture of a nutritional composition for providing nutrition to an infant. In other words the invention concerns a composition or nutritional composition comprising BGOS A and B according to the present invention for use in providing nutrition to an infant or for use in feeding an infant.

The present composition comprising BGOS A and B can advantageously be used to increase the Th1 response, increase the Th1/Th2 balance, restore imbalance in the Th1/Th2 responses, maintain a favorable Th1/Th2 balance and/or for the treatment and prevention of disorders which are associated with a Th1/Th2 imbalance. Hence, compositions which are advertised to e.g. simulate maturation of the immune system, enhance the resistance to pathogens by enhancing the immune system and/or support the immune system are part of the present invention. In a further aspect, the present invention provides a method for the treatment and/or prevention of an immune system related disorder, said method comprising administering to said mammal a composition comprising a therapeutically effective amount of the present composition comprising BGOS A and B. In a further aspect, the present invention provides a method of enhancing the immune response in a mammal said method comprising administering to the mammal the present composition comprising BGOS A and B.

The immune system of newborn human infants is characterized by an excess of Th2 response. During maturation of the immune system, the Th1 response increases and the Th1/Th2 balance shifts to values observed for healthy adults. Hence, the present combination is especially advantageous for human infants. The present invention supports the maturation of the immune system in infants. In a further embodiment, the method of the invention relates to the administration of the present composition comprising BGOS A and B to humans in the age of 0 to 6 years, preferably in the age of 0 to 4 years, preferably in the age of 0 to 2 years, more preferably in the age of 0 to 1 year. In a preferred embodiment the present method relates to the stimulation of the maturation of the immune system in human subjects in the age of 0-6 years, preferably in the age of 0 to 4 years, preferably in the age of 0 to 2 years, more preferably in the age of 0 to 1 year.

A too low Th1/Th2 balance leads to extreme sensitivity towards foreign components which could lead to a variety of immunological reactions, e.g. allergies and related diseases such as atopic dermatitis, asthma, food allergy, allergic rhinitis (e.g. pollen allergy), dust mite allergy and other forms of hypersensitivity like systemic anaphylaxis and acute urticaria. Hence, the present composition comprising BGOS A and B is especially advantageous for treatment and/or prevention of a disorder selected from the group consisting of allergy, food allergy, atopic dermatitis, asthma, allergic conjunctivitis, allergic rhinitis, dust mite allergy and urticaria. The present composition comprising BGOS A and B increases the Th1/Th2 balance.

An increase in Th1 response leads to an increase in the response against pathogenic bacteria and/or viruses. Hence, the present composition comprising BGOS A and B is suitable for the treatment and/or prevention of infections. The present composition comprising BGOS A and B can be advantageously used for the treatment and/or prevention of intestinal infections, diarrhea, intestinal inflammation, systemic infections and/or respiratory tract infections.

It was also found that the present combination can suitably be used to support vaccination processes, e.g. enhance the effects of a vaccination process. The present combination is suitable for supporting vaccination response before, during and/or after vaccination. Hence, the present composition comprising BGOS A and B is advantageously used in the treatment and/or prevention of infections, and/or for use in enhancement of vaccination response.

Hence, the present combination is advantageous for human subjects suffering from immune deficiencies, in particular elderly humans suffering from immunosenescence, humans suffering from AIDS or being infected with the Human Immunodeficiency Virus, and/or cancer patients, more particular cancer patients that are or have been subjected to chemotherapy, radiation and cancer patients that are cachectic.

The present combination is advantageously used for nutrition for elderly. Elderly have a decreased Th1 response. Elderly are especially vulnerable to viral infection complications. In a preferred embodiment the present composition comprising BGOS A and B is used for treatment and/or prevention of immunosenescence in elderly. In one embodiment, the present invention concerns providing nutrition to an elderly person. An elderly person is a person having an age of 55 years or more, in particular of the age of 65 or more.

Thus in various embodiments, the present invention concerns the use of a composition comprising BGOS A and B according to the present invention for the manufacture of a composition, preferably a nutritional composition, for
- stimulating the immune system,
- enhancing vaccination response,
- preventing and/or treating of a disease selected form the group consisting of asthma, allergy, atopic dermatitis, allergic conjunctivitis, dust mite allergy, urticaria and allergic rhinitis,
- use in preventing and/or treating of a disease selected form the group consisting of infections, diarrhea, and intestinal inflammation,
- improving the immune system, said improvement being selected from the group consisting of increasing Th1 response, increasing Th1/Th2 balance, and decreasing Th2 response,
- treating and/or prevention of immunosenescence in elderly humans
- HIV and/or AIDS patients,
- cancer patients, in particular cancer patients that are or have been subjected to chemotherapy and/or radiation and cancer patients that are cachectic,
- patients suffering from chronic obstructive pulmonary disease and/or
- patients suffering from diabetes.

In the context of the present invention, 'prevention' of a disease or certain disorder also means 'treatment of a person at risk' of a disease or certain disorder.

The mixture of BGOS A and B differing in linkages preferably results in an improved fermentation, and/or and an improved intestinal microbiota, preferably enriched in lactic acid producing bacteria, in particular bifidobacteria and/or lactobacilli as compared to the single components alone. Preferably increased acetate and/or lactate is formed. The production of the organic acids preferably results in lowering of the intestinal pH.

In one embodiment the invention concerns the use of a composition comprising BGOS A and B according to the present invention for the manufacture of a composition, preferably a nutritional composition, for use in improving intestinal microbiota. Preferably intestinal microbiota is improved by increasing the amount and/or activity of lactic acid producing bacteria. Preferably the lactic acid producing bacteria are selected from the group consisting of bifidobacteria and lactobacilli.

EXAMPLES

Example 1

Improved Effect of BGOS A and B on Th1 Response Increase

Methods:

The effect of diets comprising (a) a combination of BGOS A and fructo-oligosaccharides (b) BGOS B and (c) a combination of BGOS A and B and fructo-oligosaccharides were tested in a mouse model wherein a response to an antigen is measured by a delayed-type hypersensitivity (DTH) response. This DTH response in the ears after local challenge with an antigen present in a vaccine is a measure of Th1 cell proliferation. During response to infection and/or vaccination Th1 cells proliferate in response to the challenge with the antigen. These Th1 cells infiltrate the ear when the ear is subsequently challenged with the antigen and cause swelling. Infiltration with the Th1 cells in the ear takes about 24 h and the swelling is therefore delayed. The more Th1 cells proliferated during initial vaccination and/or infection, the more DTH upon challenging with the antigen is observed.

As a source of BGOS A VIVINAL® GOS was used. Additionally fructooligosaccharides (Raftilin HP) was used. Diet (a) and (c) comprised a weight ratio non-digestible oligosaccharides from VIVINAL® GOS:FPS of 9:1 and 1 wt. % of the sum of Non-digestible oligosaccharides from VIVINAL® GOS and FPS based on total weight of the mouse diet. VIVINAL® GOS comprises at least 67 wt % BGOS A, the rest being mainly non-digestible Gal-Glu disaccharides. Diet (b) and (c) comprised as a source of BGOS B a preparation obtained after incubation of lactose with *S. thermophilus* strain CNCM I-1620 in a method as disclosed in FR2723960 example 4. Of this preparation was 3 wt %. was added based on weight of total diet. The amount of a BGOS in this preparation was about 245 mg/g. The amount of BGOS B was about 223 mg/g, the remaining BGOS being BGOS A. The remainder of the preparation mainly comprised lactose and non-digestible Gal-Glu disaccharides. Of the BGOS the majority consisted of trisaccharides (about 88%) and tetrasaccharides (about 12 wt. %).

Female, 6 weeks old C57Bl/6 mice (Harlan Nederland BV, Horst, the Netherlands) were group-housed under a regular 12 hours light/dark regime. Group size was 10 animals per group and 3 animals in the negative control groups. The animals were given semi-synthetic diets (Research Diet Services, Wijk bij Duurstede, the Netherlands). Control diets were made to the AIN93β specifications (Reeves et al (1993) J Nutrition 123 (11): 1923-31), oligosaccharide supplemented diets were based on these specifications.

Vaccinations were started after a period of 20 days of adaptation to the new housing and diets. At day 0, a blood sample was collected prior to vaccination. At day 1, the first vaccination was administered subcutaneously. After three weeks, a booster vaccination was given (day 22). Nine days after booster injection (day 31), basal ear thickness was measured with a Digimatic outside micrometer (Mitutoyo, Veenendaal, the Netherlands) and a delayed-type hypersensitivity (DTH) response was induced by injecting antigen solution i.c. (intracutaneous) in the mouse ear pinnae. 24 h thereafter (day 32), the DTH response was measured, a blood sample was taken and the mice were sacrificed. The result obtained is the ear thickness after 24 h subtracted with the ear thickness at t=0.

The vaccinations consisted of a 100 µl i.c. (intracutaneous) injection of a 1:1 mix of antigen solution and STIMUNE® adjuvant (Specol, Cedi-diagnostics BV, Lelystad, the Netherlands). The antigen solution was a 1:100 dilution of INFLUVAC® 2002/2003 (Solvay Pharmaceuticals, Weesp, the Netherlands) in PBS. INFLUVAC® is a trivalent protein vaccine, containing 3×30 llg/ml haemagglutinin of three different influenza strains. For the DTH responses, mice were i.c. injected with 25 µl dialysed INFLUVAC® in both ears as a DTH challenge Results:

The diets containing a combination of 1 wt. % BGOS A induced a statistically significant increase of 100% in the DTH response (see Table 1). BGOS B also induced a statistically significant increase of 112% in the DTH response.

Surprisingly a combination of BGOS A and B showed the highest response increase of 192%.

These results are indicative for a further improved effect, provided by the administration of BGOS A and BGOS B on Th1 response increase

TABLE 1

| | DTH response | | |
|---|---|---|---|
| Group: | Mean DTH µm (S.E.) | Δ DTH µm | Relative DTH |
| Sham | 24.3 (0.6) | 0 | 0 |
| Placebo | 66.5 (0.3) | 42.2 | 1.00 |
| Group a BGOS A | 108.9 (0.3)* | 84.6 | 2.00 |
| Group b BGOS B | 113.6 (0.3)* | 89.3 | 2.12 |
| Group c BGOS A + B | 147.6 (0.2)*a | 123.2 | 2.92 |

*$p < 0.05$ compared with placebo
a$p < 0.05$ compared with group a and b

The results of this experiment are an indication that the present invention can advantageously be used for support in vaccination response. The results of this experiment are also an indication that it can advantageously be used in subjects with a low Th1 response, in particular infants. The results of this experiment are also an indication that it can advantageously be used in subjects with a low Th1 response, in particular elderly suffering or at risk for suffering from immunosenescence, HIV patients, AIDS patients and/or cancer patients that are or have been subjected to chemotherapy and/or radiation or that are cachectic, patients suffering from COPD and/or patients suffering from diabetes. This model is indicative for basic immunological changes, which can be beneficial in all disorders with malfunctioning immune system. It is known that infants, elderly, HIV infected, cancer patients, COPD patients and/or diabetes patients have an immune system that does not function at full capacity. For all the above is an additional help possibly beneficial.

Example 2

Infant Milk Formula

An infant formula was prepared by using as ingredients skim milk, whey protein, lactose, vegetable fat, minerals, vitamins and trace elements as known in the art. As a source of BGOS B a preparation obtained after incubation of lactose with *S. thermophilus* strain CNCM I-1620 in a method as disclosed in FR2723960 example 4 and also described in example 1 was used. The final concentration based on dry weight of the total composition infant formula was 5.4 wt. %. As a source of BGOS A VIVINAL® GOS was used. Additionally fructooligosaccharides (RAFTILIN HP®) was used.

The ingredients were pasteurized, mixed, homogenize, sterilized and spray dried to a powder as known in the art.

Final composition of the infant formula after reconstitution to a ready to drink formula comprised per 100 ml:

68 kcal 1.45 g protein (casein and whey protein from milk; partially hydrolysed)

8.6 g digestible carbohydrates (mainly lactose and maltodextrin)

3.1 g fats (mainly vegetable fats)

0.8 g comprising non digestible oligosaccharides of which 0.08 g fructooligosaccharides (source RAFTI-LIN HP®)

of which 0.22 g non digestible oligosaccharides formed by the *S. thermophilus* strain (about 73 wt. % BGOSB, 07.3 wt. % BGOS A and the rest Gal-Glu non-digestible disaccharides)

of which 0.5 g non digestible oligosaccharides as present in VIVINAL® GOS (at least 67 wt. % BGOSA, the rest mainly Gal-Glu non-digestible disaccharides)

Trace elements, minerals, vitamins and other micronutrients (taurine, choline, inositol, nucleotides, carnitine) as known in the art.

The invention claimed is:

1. A nutritional composition comprising at least two different beta-galacto-oligosaccharides A and B wherein
   (a) A has the structure of $Gal_n$-Glu and/or $Gal_m$, with n=2 to 6 and m=2 to 7, wherein the sum of beta 1,4 and beta 1,6 linkages represents at least 80% of the total number of linkages between galactose residues in A, and
   (b) B has the structure of $Gal_n$-Glu and/or $Gal_m$, with n=2 to 6 and m=2 to 7, wherein beta 1,3 linkages represents at least 80% of the total number of linkages between galactose residues in B,
   (c) the weight ratio of A:B is between 1:1 and 5:1; and
   (d) the sum of beta-galacto-oligosaccharides A and B is 250-2500 mg per 100 ml of the nutritional composition.

2. The composition according to claim 1, wherein the sum of beta-galacto-oligosaccharides A and B represents at least 1 wt. % of the dry weight of the composition.

3. The composition according to claim 1, further comprising fructo-oligosaccharides.

4. The composition according to claim 1, further comprising 5 to 50% protein, 15 to 85% carbohydrates and 5 to 50% lipid based on calories.

5. The composition according to claim 1, further comprising non-viable or living *Bifidobacterium breve*.

6. The composition according to claim 5, comprising $10^3$ to $10^{13}$ cfu living *B. Breve* or the equivalent of non-viable *B. breve* per gram dry weight of the present composition.

7. An infant formula composition comprising the composition according to claim 1.

8. The composition according to claim 2, wherein the sum of beta-galacto-oligosaccharides A and B represents at least 4 wt. % of the dry weight of the composition.

9. A method of stimulating the immune system, comprising administering to a human subject the composition according to claim 1.

10. The method of claim 9, wherein the human subject is a human infant.

11. A nutritional composition comprising a non-digestible oligosaccharides component, wherein the non-digestible oligosaccharides component consists of:
   (a) at least two different beta-galacto-oligosaccharides A and B, wherein beta-galacto-oligosaccharide A has the structure of $Gal_n$-Glu and/or $Gal_m$, with n=2 to 6 and m=2 to 7, wherein the sum of beta 1,4 and beta 1,6 linkages represents at least 80% of the total number of linkages between galactose residues in A, and wherein beta-galacto-oligosaccharide B has the structure of $Gal_n$-Glu and/or $Gal_m$, with n=2 to 6 and m=2 to 7, wherein beta 1,3 linkages represents at least 80% of the total number of linkages between galactose residues in B, and
   (b) optionally fructo-oligosaccharides.

12. A nutritional composition comprising:
   (a) at least two different beta-galacto-oligosaccharides A and B, wherein beta-galacto-oligosaccharide A has the structure of $Gal_n$-Glu and/or $Gal_m$, with n=2 to 6 and m=2 to 7, wherein the sum of beta 1,4 and beta 1,6 linkages represents at least 80% of the total number of linkages between galactose residues in beta-galacto-oligosaccharide A, and wherein beta-galacto-oligosaccharide B has the structure of $Gal_n$-Glu and/or $Gal_m$, with n=2 to 6 and m=2 to 7, wherein beta 1,3 linkages represents at least 80% of the total number of linkages between galactose residues in beta-galacto-oligosaccharide B,
   (b) 5 to 50% protein, 15 to 85% carbohydrates and 5 to 50% lipid based on calories,
   (c) minerals, vitamins and trace elements,
   (d) optionally non-viable or living *Bifidobacterium breve*,
   (e) optionally fructo-oligosaccharides, and
   (f) in case the composition is in liquid form, water.

13. A method of increasing Th1 response, comprising administering to a human subject the composition according to claim 1.

14. The method of claim 13, wherein the human subject has a disease selected form the group consisting of infections, diarrhea, and intestinal inflammation.

15. The method of claim 13, wherein the human subject has a disease selected from the group consisting of asthma, allergy, atopic dermatitis, allergic conjunctivitis, dust mite allergy, urticaria and allergic rhinitis.

16. A method of improving intestinal microbiota by increasing the amount and/or activity of lactic acid producing bacteria, comprising administering to a human subject the composition according to claim 1.

17. The method of claim 15, wherein the human subject is a Human Immunodeficiency Virus ("HIV") and/or Acquired Immunodeficiency Syndrome ("AIDS") patient.

18. The method of claim 15, wherein the human subject is a cancer patient.

19. The method of claim 18, wherein the cancer patient is cachectic.

20. The method of claim 15, wherein the human subject suffers from chronic obstructive pulmonary disease.

21. The method of claim 15, wherein the human subject suffers from diabetes.

22. The method of claim 13, wherein the human subject is an elderly human subject suffering from immunosenescence.

* * * * *